United States Patent
Aycock et al.

(10) Patent No.: US 11,508,466 B2
(45) Date of Patent: Nov. 22, 2022

(54) METHODS, SYSTEMS, AND DEVICES FOR DETERMINING MULTI-PARTY COLLOCATION

(71) Applicant: CERNER INNOVATION, INC., Kansas City, KS (US)

(72) Inventors: Daniel Aycock, Kansas City, MO (US); Mario Manese, Kansas City, MO (US); Colin Wurtz, Prairie Village, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 173 days.

(21) Appl. No.: 16/152,157

(22) Filed: Oct. 4, 2018

(65) Prior Publication Data

US 2019/0172567 A1 Jun. 6, 2019

Related U.S. Application Data

(60) Provisional application No. 62/594,467, filed on Dec. 4, 2017.

(51) Int. Cl.
| | | |
|---|---|---|
| *G16H 10/60* | (2018.01) | |
| *G06N 5/02* | (2006.01) | |
| *G16H 40/20* | (2018.01) | |

(52) U.S. Cl.
CPC ............ *G16H 10/60* (2018.01); *G06N 5/022* (2013.01); *G16H 40/20* (2018.01)

(58) Field of Classification Search
CPC ......... G16H 10/60; G16H 40/20; G06N 5/022
USPC ............................................................ 705/2
See application file for complete search history.

(56) References Cited

U.S. PATENT DOCUMENTS

| | | | |
|---|---|---|---|
| 10,015,756 B1* | 7/2018 | Bullington | H04W 16/20 |
| 2009/0076346 A1* | 3/2009 | James | A61B 5/282 |
| | | | 600/301 |
| 2011/0105854 A1* | 5/2011 | Kiani | G16Z 99/00 |
| | | | 600/300 |
| 2015/0213217 A1* | 7/2015 | Amarasingham | G16H 50/30 |
| | | | 705/2 |
| 2015/0347705 A1* | 12/2015 | Simon | G16H 10/60 |
| | | | 705/3 |
| 2016/0249174 A1* | 8/2016 | Patel | A61B 5/01 |

OTHER PUBLICATIONS

J. K. Ng, J. Wang, K. Lam, C. H. C. Kam and S. Han, "Capturing and Analyzing Pervasive Data for SmartHealth," 2014 IEEE 28th International Conference on Advanced Information Networking and Applications, Victoria, BC, 2014, pp. 985-992, doi: 10.1109/AINA.2014.119. (Year: 2014).*

* cited by examiner

*Primary Examiner* — Christopher L Gilligan
*Assistant Examiner* — Bennett Stephen Erickson
(74) *Attorney, Agent, or Firm* — Shook, Hardy & Bacon L.L.P.

(57) ABSTRACT

Methods, systems, and computer-readable media are provided for analyzing amounts of time spent by clinicians caring for patients. Clinician locations, patient locations, patient data, and clinician electronic health record activity may be used to facilitate generation of one or more predictive models. Such predictive models will provide, among other things, a decision support tool for scheduling patient-clinician appointments to minimize, at least partially, patient wait times.

20 Claims, 12 Drawing Sheets

500

| Appt Time | Reason For Visit | Appt Type | Sch Duration |
|---|---|---|---|
| 5/23/2017 1:50 pm | 18 MNTH WCC | RT 2 | 20 mins |
| 5/23/2017 2:10 pm | 2 MNTH WCC | RT 2 | 20 mins |
| 5/23/2017 2:30 pm | 12 MNTH WCC | RT 2 | 20 mins |
| 5/23/2017 2:50 pm | Wheezing | RT 1 | 10 mins |
| 5/23/2017 3:00 pm | 9 MNTH WCC | RT 2 | 20 mins |
| 5/23/2017 3:20 pm | COUGH | RT 1 | 10 mins |
| 5/23/2017 3:30 pm | 2 MO WCC | RT 2 | 20 mins |
| 5/23/2017 4:10 pm | F/U ASTHMA | RT 1 | 10 mins |

Scheduled Duration: 10 mins

| | Physician Exam Time | In-Room TiEMR | Out of Room TiEMR |
|---|---|---|---|
| Overall | 9.3 mins | 5.8 mins | 7.2 mins | 22.3 mins
| Dr. #1 | 6.6 mins | 6.5 mins | 7.0 mins | 20.1 mins
| Dr. #2 | 12.8 mins | 4.9 mins | 7.5 mins | 25.2 mins

RT2

Scheduled Duration: 20 mins

| | Physician Exam Time | In-Room TiEMR | Out of Room TiEMR |
|---|---|---|---|
| Overall | 12 mins | 7.8 mins | 6.1 mins | 27.8 mins
| Dr. #1 | 10.5 mins | 8.1 mins | 5.4 mins | 24.0 mins
| Dr. #2 | 20.7 mins | 9.3 mins | 8.8 mins | 38.8 mins

FIG. 7

METHODS, SYSTEMS, AND DEVICES FOR DETERMINING MULTI-PARTY COLLOCATION

CROSS-REFERENCE TO RELATED APPLICATIONS

This application claims the benefit of U.S. Provisional Application No. 62/594,467, entitled "METHODS, SYSTEMS, AND DEVICES FOR DETERMINING MULTI-PARTY COLLOCATION," filed Dec. 4, 2017, which is hereby incorporated by reference in its entirety.

BACKGROUND

Clinicians see multiple patients a day, often in pre-scheduled appointments. Further, clinicians access electronic health records (EHRs) multiple times within a given shift of work and even outside of their respective work shifts. The EHRs are accessed to, for example, document patient care, examine patient histories, review medications, prescribe medications, enter orders for a patient, check a status of an order, etc. While scheduled appointments and EHR documentation are necessary to provide efficient patient care, if the appointments are scheduled for too much time, the clinician's time is wasted. If appointments are scheduled for too little time a clinician spends longer than expected caring for the patient and a queue of patients waiting to be seen is created. If EHR documentation is not properly accounted for, a clinician's day is longer than necessary. Failure to identify such problems may lead to patient frustration, delayed treatment, clinician inefficiency, loss of revenue, and so on.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for analyzing, for instance, time of patient-clinician colocation, patient data, and/or clinician-EHR activity to generate predictive models for patient-clinician appointment optimization. The generated models may be implemented as a decision support tool configured to determine and recommend patient appointment durations and/or slots.

BRIEF DESCRIPTION OF THE DRAWINGS

Embodiments are described in detail below with reference to the attached drawings figures, wherein:

FIGS. 5A and 5B depict a portion of an exemplary schedule for a clinician stored in an EHR system and a GUI display, in accordance with an embodiment of the present invention;

FIG. 7 depicts a portion of output from a time analysis engine, in accordance with an embodiment of the present invention;

DETAILED DESCRIPTION

Figure 1:
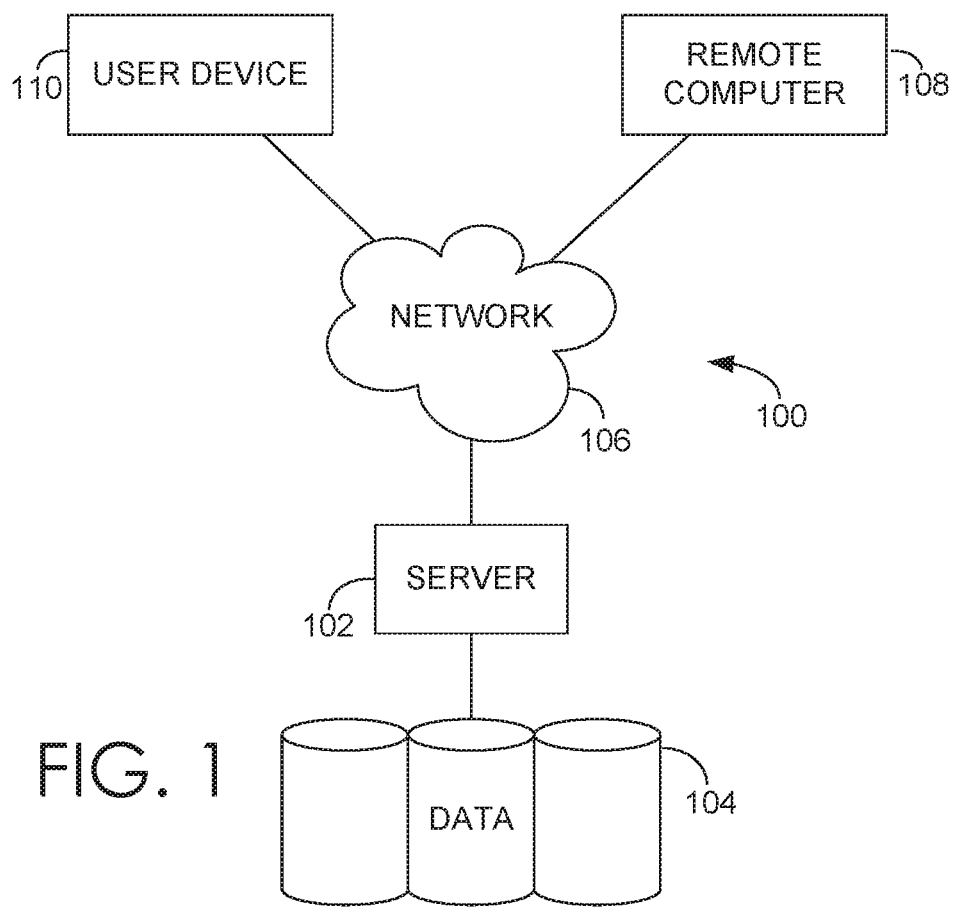
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the methods, systems, and devices described herein improve upon limitations of prior medical informatics technology by, at a minimum, removing human subjectivity previously intrinsic to the field. For instance, prior time-motion study techniques relied upon either human observation or observation of a proxy to record worker effort and/or efficiency. Both of these techniques have significant subjectivity aspects. First, human observation of work effort is inherently based on subjective human decisions. Second, human observation of work effort often, if not always, alters the behavior of the observed worker. Third, selection of a proxy reflects subjective judgments on the measure of effort and/or efficiency. Embodiments described herein replace the human subjectivity with specific rules, processes, systems and techniques.

Embodiments of the present invention are directed to methods, systems, and computer-readable media for analyzing time data. A first aspect is directed to a system comprising a wireless communication device, a plurality of wireless receivers, one or more processors, and computer readable instructions. The wireless communication device is configured to broadcast a device identifier. Each of wireless receivers is configured to receive the device identifier broadcast by the wireless communication device, determine a signal strength, and generate a time stamp associated with the receipt of the device identifier. The computer readable instructions cause the one or more processors to perform operations comprising: receiving the device identifier, the signal strengths, and the associated time stamp from a set of the plurality of wireless receivers; based on the signal strengths and the associated time stamp, determining a location of the wireless communication device at a first time; based on the location of the wireless communication device, determine that a provider associated with the wireless communication device is at the determined location; and, based on the time stamp, the determined location, and the provider determine that the provider and a patient are colocated. The system may also include an electronic health record system for storing medical information for a plurality of patients.

A second aspect is directed to one or more computer storage media having computer-executable instructions embodied thereon that, when executed, facilitate a method of time data analysis. The media includes receiving time data, the time data comprising an amount of time a set of patients and a set of clinicians were colocated; retrieving patient data for the set of patients; tuning a predictive model by supplying the predictive model the time data and the patient data corresponding to input variables in the predictive model; receiving a clinic appointment request for a particular patient; and in response to receiving the new appointment request utilizing the tuned predictive model to identify one or more recommended appointment times and durations.

A third aspect is directed to a computer implemented method for using broadcast identifiers to predictively generate optimized scheduling. The method includes receiving a plurality of device identifiers, signal strengths, corresponding time stamps, and wireless receiver identifiers from a set of wireless receivers configured to receive device identifiers broadcast by a set of devices, each device of the set of devices associated with a health care clinician; segmenting the plurality of device identifiers, signal strengths, corresponding time stamps, and wireless receiver identifiers by device identifier thereby generating a per-device set of data for each device identifier comprising a plurality of signal strengths, corresponding time stamps, and wireless receiver identifiers; determining, for each per-device set of data, a location of the device associated with the device identifier at each time stamp based on the signal strengths and the wireless receiver identifiers, thereby generating an enhanced per-device set of data; retrieving patient data for a set of patients associated with the health care provider from an electronic health records (EHRs) system, wherein the set of patients are identified at least partially based on the location of the device at each time stamp; training and/or validating a predictive model by providing the clinician locations, patient location, and patient data as training and/or validating inputs to the predictive model, the predictive model configured to identify appointment durations and appointment slots as output; receiving an appointment request for a particular patient; retrieving the particular patient's patient data from the EHR system; and, scheduling the appointment for a length of time determined by the predictive model.

As used herein, the terms "colocation" and "colocated" are used in reference to the positioning of two or more people within close proximity of each other. While nothing described herein should be construed as limiting colocation to a specific distance; given the context, those skilled in the art will understand that colocation of a clinician and patient generally means the patient and clinician are within the same room, treatment area, and/or distance reasonable to allow for patient-clinician interaction, care, observation, and/or treatment.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer-readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise transitory signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health-care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, on any of the remote computers 108, or one any of the user devices 110. For example, and not by way of limitation, various application programs may reside on the memory associated with any one or more of the remote computers 108 and/or any one or more of the user devices 110. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

The user device 110 may be personal computers, network PCs, peer devices, or the like, and may include some or all of the components described above in relation to the server 102. The devices can be personal digital assistants, smartphones, or other like devices. In some embodiments, user device 110 is a specific, purpose built, device that is discussed in detail with regards to user device 230. In some embodiments, user device 110 is a general purpose computing device operating purpose built software. In some embodiments of environment 100 user devices 110 comprise both purpose built devices and general purpose devices operating purpose built software.

Figure 2:
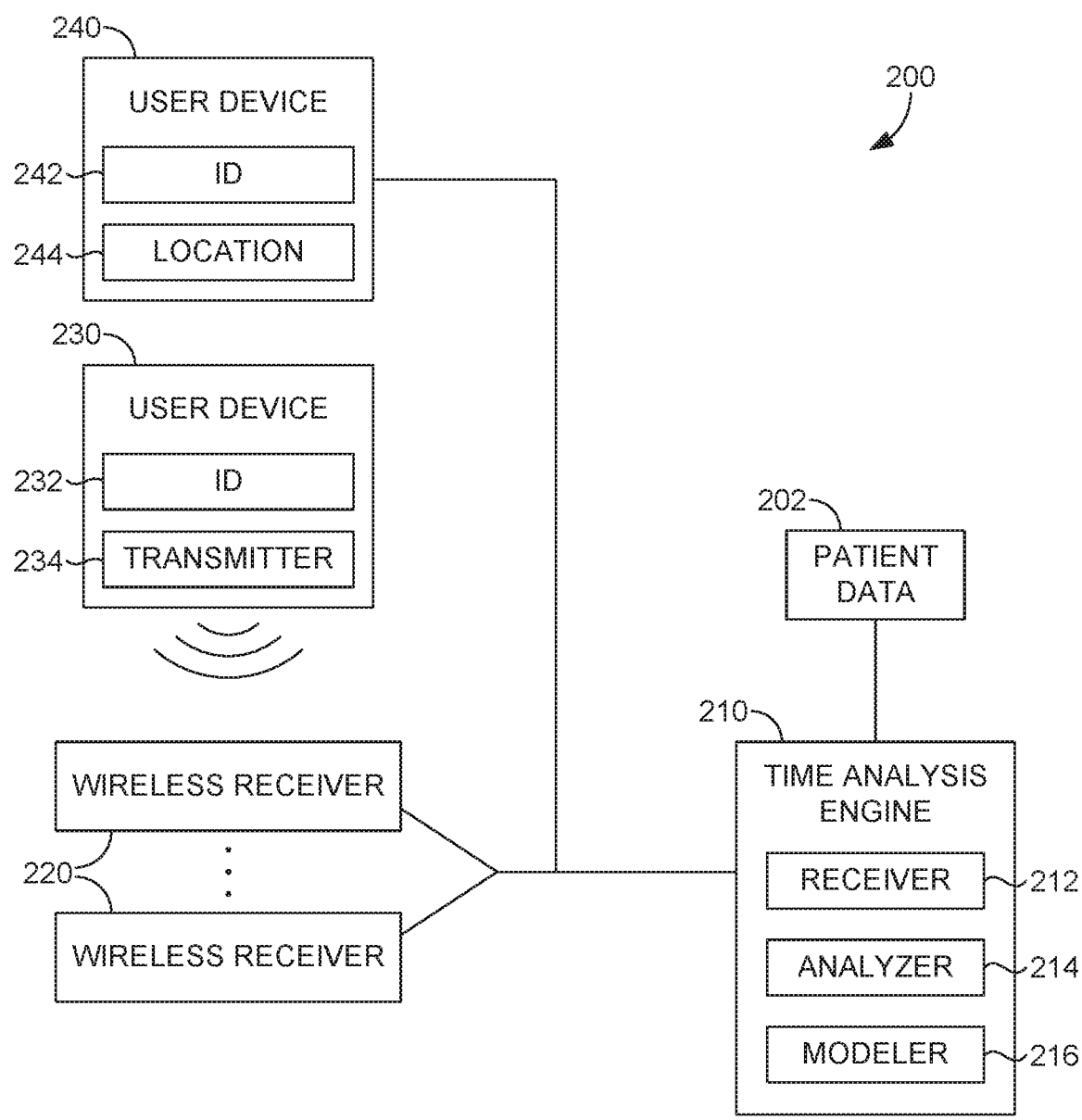
FIG. 2 is a block diagram of an exemplary computing system suitable to implement embodiments of the present invention.

Turning to FIG. 2, an exemplary system 200 with which embodiments of the present invention may be implemented is depicted. It will be understood and appreciated by those of ordinary skill in the art that the illustrated medical information computing system 200 is merely an example of one suitable computing environment and is not intended to suggest any limitation as to the scope of use or functionality of the invention. Neither should the medical information computing system 200 be interpreted as having any dependency or requirement relating to any single component or combination of components illustrated therein.

Generally, system 200 may comprise patient data 202, a time analysis engine 210, and user devices (such as user device 230 and/or user device 240). Some embodiments of system 200 may further comprise wireless receivers 220. Patient data 202 generally includes any and all information related, directly and/or indirectly, to patient care stored in an electronic health records (EHR) system of a health care provider, a network of health care providers, institutions, and/or a network of institutions. For instance, patient data may include, but is not limited to, an individual health record for each patient, metadata, and appointment scheduling information. A health record may contain patient demographics data, such age, gender, height, weight, medication history, primary language identifiers; clinician(s) responsible for patient care; diagnosis information; patient complaints; insurance information; laboratory test results; image studies (e.g. X-Ray, CT-Scan, MRI studies, and the like); clinician notes; and so on. Further, the health record may contain similar data recorded at various times; such as previous appointments; emergency room visits; surgeries; therapy sessions; urgent care visits; and so on. Additionally, the health record may contain data recorded in other EHR systems at other health care providers, health care provider networks, institutions, and/or institution networks. This data can be stored in a variety of different formats such as unstructured text, structured text, images, buttons, automatically populated fields, graphs, and so on. Patient data 202 may be stored in one or more data clusters, such as data cluster 104.

Metadata may comprise any data captured and/or tracked by the EHR system which does not directly relate to patient care. For example, a time stamp and clinician identification when a remote computer opens, modifies, edits, and/or closes a patient EHR. Further, the metadata may indicate the remote computer from which the clinician opened, modified, edited, and/or closed a patient EHR. In some embodiments, metadata tags are created by the EHR for each activity (opening, modifying, editing, closing, and/or the like). The metadata tags may also include category tags (indicating a category description) or activity tags (indicating an activity description). For instance, a category tag may identify a particular clinician or area of specialty associated with the active indication. An activity tag may identify the activity performed such as order entry. A clinician identification may be captured by the EHR through any suitable means. For example, the EHR may require the clinician to log in to the EHR by providing a unique ID, password, and/or scanning an ID card. As the clinician interacts with the EHR by, for example, entering new test results, accessing notes from a previous appointment, and so on, the EHR may store a record of those interaction as metadata.

Appointment scheduling information generally includes any recorded information related to the location, date and time, motivation, and duration of an appointment. This may comprise appointment time (scheduled Dt/Tm); scheduled duration; a reason for visit; room assignment; and so on for a specific patient. Appointment time may for example refer to the scheduled time of the appointment. The scheduled duration may refer to the overall expected (scheduled) duration of the appointment and/or the expected (scheduled) duration of the constituent parts of the appointment. For example, the scheduled duration may reflect that the patient's appointment, overall, is scheduled to take 20 minutes. Additionally, and/or alternatively, the scheduled duration may reflect that the patient check-in is scheduled to take 2 minutes, the first clinician-patient interaction (for example nurse-patient) is scheduled to take 7 minutes, the second clinician-patient interaction (for example primary care physician-patient) is scheduled to take 10 minutes, and patient check-out is scheduled to take 1 minute. It will be understood by those skilled in the art that this is merely an illustrative example.

The appointment scheduling information may also indicate the overall availability of clinicians. For instance, clinician 1 may be available for patient appointments from 8:00 am until 11:00 am on Monday's; unavailable on Tuesday's; available from 7:30 am until 9:00 am and from 1:00 pm until 5:25 pm on Wednesday's; and so on. Clinician 2 may be available from 9:00 am until 1:00 pm on Monday's; unavailable on Tuesday's; available from 9:30 am until 11:00 am and from 1:00 pm until 5:25 pm on Wednesday's; and so on. It will be understood by those skilled in the art that this is intended as merely an illustrative example. The appointment scheduling information may also indicate any clinician-clinician associations that may exist. For example, clinician 1 may be a physicians' assistant who is associated with (works with) clinician 2, clinician 15, and clinician 6.

The time analysis engine 210 generally receives data from the other components (such as patient data 202, user device 230 and/or 240, and wireless receiver 220), analyzes the received data, generates, validates, and/or trains a predictive model. In an embodiment, once generated the model is stored as a discrete analytic tool for later use by the health care provider, health care provider network, or any other entity. In an embodiment, the generated, validated, and/or trained model may be incorporated into the EHR system as a decision support tool to schedule appointments. Although the time analysis engine 210 is discussed herein with discretely identified subcomponents it will be understood by those skilled in the art that this is not intended to limit the scope of the invention described herein. Rather, it is contemplated by the inventors that the operations may be performed in a distributed computing environment, operations identified as being performed by a subcomponent may be performed by other subcomponents and/or components.

The receiver component 212 is configured for, among other things, receiving (or retrieving) patient data 202, user device data, wireless receiver data, and so on. The patient data 202, including individual health records, metadata, and appointment scheduling information may be received from an EHR communicatively coupled to the time analysis engine 210. The user device data, including a device identifier, signal strengths, corresponding time stamps, and/or wireless receiver identifiers, may be received by the receiver component 212 from a user device, such as user device 240, and/or a wireless receiver, such as wireless receiver 220. For instance, FIG. 5 provides an exemplary view of a subset of appointment scheduling information 502 received from an EHR communicatively coupled to a time analysis engine, such as time analysis engine 210. In this example, that was obtained on May 23, 2017 and depicts the deidentified portion of a single clinician's scheduled appointments from 1:50 pm through 4:10 pm; the reason for each appointment (for example an 18 month well child care appointment, a 2 month well child care appointment, a patient complaint of wheezing, and so on); an appointment type (RT 2 or RT 1); and a scheduled duration.

Returning to FIG. 2; in embodiments, the receiving component 212 may receive data provided by other components of the system 200. For instance, wireless receiver 220 may be configured to continuously, periodically, and/or intermittently communicate data to the receiver component 212. In some embodiments, the receiving component 212 may request data continuously, periodically, and/or intermittently, from other components of the system. For instance, the receiving component may generate computer readable instructions that comprise instructions requesting that data be sent to the receiving component 212. Further, the receiving component 212 may access data continuously, periodically, as needed, and/or intermittently. For example, the analysis component may instruct the receiving component to access patient data 202 user device data, and/or wireless receiver data.

The analyzer component 214 generally analyses the data received by the time analysis engine 210. For instance, the analyzer component 214 may determine clinician and/or patient locations at one, more than one, and/or a plurality of time points. In some embodiments, the analyzer component 214 determines a clinician location based on data received from a user device. For instance, a user device, such as user device 230, may be configured to repeatedly broadcast a unique device identifier. Wireless receivers, such as wireless receiver 220, may receive the device identifier; generate a time stamp corresponding to the time at which the receiver received the broadcast; and generate a numerical representation of the signal strength associated with the device identifier broadcast. The analyzer component may identify the wireless receiver that received the device identifier at the first (earliest) time stamp; determine a location associated with the wireless receiver; and determine that the device associated with the device identifier was located at the location associated with the wireless receiver at the first time stamp. A similar process may be applied to determine the user devices location at the second time stamp, the third time stamp, the fourth, and so on. FIG. 6 provides an exemplary view of a subset of clinician locations 602 determined based on information received from a set wireless receivers, such as wireless receiver 220, as a clinician carrying a user device moved throughout the day.

In some embodiments, the analyzer component 214 may pre-process data used to determine a clinician's location. For instance, in a system with a plurality of wireless receivers (such as wireless receiver 220) it is possible that multiple wireless receivers will detect the device identifier broadcast by a specific user device (such as user device 230) at any given time. As such, in an embodiment, the analyzer component 214 pre-processes the raw signal strengths for each wireless receiver that received the same device identifier at the same (or substantially the same) time. For instance, pre-processing may include determining the geometric, arithmetic, and/or weighted arithmetic mean of the raw signal strengths for a predetermined number of previous and/or subsequent time stamps reported by each wireless receiver. The geometric, arithmetic, and/or weighted arithmetic means may be compared. The value corresponding to the strongest signal may be identified as the wireless receiver location for the time stamp and the location of the device may be determined to correspond to the wireless receiver location.

In some embodiments, the clinician's location is determined by the user device, such as user device 240. For instance, the user device 240 may determine its own location based on: triangulation of cellular, WiFi, or similar signals; signals detected from GPS, GLONASS, Galileo, BeiDou-2, or similar satellite based systems integrated into the user device; or any other suitable location determination system.

The analyzer component 214 may identify patient locations in a variety of ways. In some embodiments, metadata associated with the patient data 202 is used by the analyzer component to determine the location of a patient. For example, when the patient arrives for an appointment, an indication may be made in the patient's electronic health record that the patient has arrived, at $T_x$, for their schedule appointment. The metadata associated with this entry may indicate the time the entry was made and/or the remote computer, such as remote computer 108, at which the entry was made. In some embodiments, the analyzer component 214 determines a patient location has changed from one location to another location in response to detecting at least one of a set of predetermined actions within the patient's EHR. For instance, the first set of predetermined actions may comprise the first occurrence of a clinician opening the patient's EHR after the patient has completed check-in and/or registration. The analyzer component 214 may detect the time stamp associated with a metadata tag indicating a clinician opened the patient's EHR, at $T_y$, and determine that the patient location has changed. Additionally, and/or alternatively, the first set of predetermined actions may comprise the entry of the first clinical event, vital signs, family history, social history, medical procedure history, general medical history, medication history, or any other indication within the patient's electronic health record indicative of an initial interaction between the patient and a clinician.

Further, the analyzer component 214 may determine the amount of time a clinician spends in an EHR for a patient and the location of that clinician during that time. In an embodiment, the location of the clinician is based on the location of the remote computer the clinician uses to access the EHR and/or the location of a user device, such as user device 230 and/or 240, associated with the clinician at the time the EHR was being accessed. For example, a remote computer, such as remote computer 108, may access patient data, such as patient data 102. The metadata associated with the remote computer accessing the patient data may indicate a specific remote computer (by for example MAC address, IP address, or any other suitable means). The metadata may indicate a specific clinician and/or clinician ID that is associated with the remote computer and the access. Further the metadata may indicate a time associated with the access. Additionally, and/or alternatively, the user device 230 and/or 240 associated with the clinician may indicate that the clinician was at a specific location while the patient data was accessed. In some embodiments, the analyzer component 214 may identify the total amount of time a clinician spent in the EHR and/or identify the amount of time a clinician spent in the EHR while colocated with the patient and the total amount of time the clinician spent in the EHR while not colocated with the patient. In other words, by segmenting the patient data by clinician and time the total time spent in the EHR of the patient may be calculated by the analyzer component. By segmenting the patient data by clinician, time, patient location, and clinician location and/or remote computer location the total time in the EHR while colocated with the patient and/or the total time in the EHR while not colocated with the patient may be calculated by the analyzer.

Further, the analyzer component 214 may distinguish between active time in the EHR and inactive time. Active time, as used herein, refers generally to time spent performing one or more activities and having an active indication no more than a predetermined time interval away from another active indication. Active indications include, but are not limited to, keystrokes (e.g., typing in a keyboard or typing on a touch screen), clicks (e.g., by a mouse), mouse miles (e.g., movement of the mouse), touch screen selections (e.g., any selection of a touch screen), and the like. Thus, a first active indication can be no more than a predetermined time interval away from a second active indication in order to have the time between counted as active time. The analyzer component 214 may monitor the time intervals and compare to a predetermined time interval to classify time as active or inactive. The analyzer component 214 may also identify metadata tags for each active indication associated with various information including a time stamp for each activity, active indications for each activity, and the like.

The analyzer component 214 may also identify relevant categories of patient data for use by the modeler component 216. The analyzer component 214 may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages. For example, the R-package leaps may be utilized for the identification of relevant patient data, by performing an exhaustive search for the best subset(s) of the variables in the patient data, such as patient data 202, for predicting variations in duration of patient appointments, variations in the duration of clinician-patient colocation, variations in scheduled duration versus actual duration, and/or duration and location of clinician-EHR activity. Once identified, the relevant categories of patient data may be used to generate one or more predictive models.

Modeler component 216 generally generates, validates, and/or trains one or more predictive models. Modeler component 216 may generate the predictive model by identifying a set of available variables from the data provided to or otherwise accessible by the time analysis engine 210. For instance, the set of available variables may comprise any and/or all categories of patient data 202. Additionally, and/or alternatively, the set of available variables may comprise the categories of patient data 202 determined to be statistically correlated to variations in duration of patient appointments, variations in the duration of clinician-patient colocation, variations in scheduled duration versus actual duration, and/or duration and location of clinician-EHR activity. Further modeler component 216 may identify a set of attributes for each variable. In an embodiment, the set of attributes may comprise actual values acquired from the patient data 202 corresponding to the variables. In an embodiment, the set of attributes may comprise random (or pseudorandom) values for each variable.

Additionally, the modeler component 216 may identify a set of events that approximate the activity of the appointment. For example, an appointment can be modeled as five discrete events, patient arrival, a first clinician-patient interaction (for instance a nurse-patient interaction), a second clinician-patient interaction (for instance a physician-patient interaction), clinician-EHR activity, and patient departure. In an embodiment, the set of events is predefined based on the health care provider's practices. For instance, the health care provider may identify their ideal appointment as comprising check-in, a single clinician-patient colocation event (physician-patient interaction), and patient departure. In an embodiment, the set of events is determined based on interactions identified by the time analysis engine 210. For instance, the time analysis engine 210 may determine that a statistically significant majority of appointments comprise a check-in event, a first clinician-patient colocation event, a second clinician-patient colocation event, and a check-out event.

Further, modeler component 216 may generate at least one predictive model based on the identified variables, events, and attributes. In some embodiments, the predictive model is a discrete event simulation. For example, a predictive model may be generated that represents a first discrete event (e.g. patient arrival) as creation of an entity (patient) with a set of attributes. In an embodiment, the attributes are randomly or pseudo randomly assigned to the patient. For instance, the model may create a patient with the number of active patient complaints with a first randomly assigned value, the number and recency of emergency and urgent care visits with a second randomly assigned value, documented medications with a third randomly assigned value, and so on. In an embodiment, the attributes are assigned to the patient at a rate corresponding to the rate of actual occurrence in the patient population of the health care provider. In an embodiment, a clinician resource may then be assigned to the entity. The clinician resource may have attributes assigned as well. The model may move entities from the first event to the second event (e.g. first clinician-patient colocation event). Then, move the entities from the second event to the third event (e.g. second clinician-patient colocation event), and so on. Further, the modeler component 216 may train, hone, and/or validate the generated model by supplying the duration of clinician-patient colocation, duration of clinician-EHR activity, patient data, and so on as predetermined input sets. In some embodiments, a predictive model may be a Markov process, such as a Markov chain. For example, a series of states may be generated that represents the phases of the patient's appointment. A patient may be generated and assigned attributes. The probability of moving from one state to another through the appointment may be a weighted function of the attributes assigned to each patient. In an embodiment, the modeler component may store generated predictive models in a computer readable storage medium (not depicted).

Wireless receiver 220 generally receives device identifiers, such as device identifier 232, broadcast by the transmitting component 234 of the user device, such as user device 230. Further, wireless receiver 220 communicates the device identifiers, signal strength, corresponding timestamps, and a wireless receiver identifier to the time analysis engine 210. In some embodiments, wireless receiver 220 is configured to continuously, periodically, and/or intermittently communicate data to the time analysis engine 210. In some embodiments, a wireless receiver is assigned a location corresponding to a room, area, or region of a health care provider's facility. For instance, wireless receiver 1 may be assigned a location corresponding to clinic room 101, wireless receiver 2 may be assigned to clinic room 102, and so on. It will be understood by those skilled in the art that the preceding is merely an illustrative example, not meant to limit the scope of the embodiments described herein. For instance, wireless receivers may also be assigned to non-clinic rooms such as nurses' stations, lounges, office rooms, emergency rooms, and so on. Further, multiple wireless receivers may be assigned to a single room.

Generally, user devices 230 and 240 are associated with, assigned to, or otherwise correspond to a specific clinician. In some embodiments, this association is merely temporary. For example, a clinician may choose a user device 230 from a pool of user devices. The specific user device 230 selected by the clinician may then be associated with the clinician through any suitable means. For example, in an embodiment the user device may be associated with the clinician by assigning the clinician the device identifier associated with the user device in a database (not depicted) communicatively coupled to time analysis engine 210. The clinician may return the user device 230 to the pool and the association between the clinician and the device may be removed. The clinician may select a second user device and then be associated with the device identifier for the second device. In some embodiments, the association between a user device and a clinician is, in all relevant ways, permanent. For instance, clinician may own the user device. For example, the clinician's smartphone may be a suitable user device. An application may be installed on the smartphone which enables communication between the clinician's smartphone and the time analysis engine 210. The application may assign the smartphone a device identifier and/or use an already existing unique identifier associated with the smart phone as the device identifier.

User device 230 generally broadcasts a device identifier, which is received by one or more wireless receivers, such as wireless receiver 220. Further, user device 230 may take on a variety of forms, such as a personal computer, a laptop computer, a tablet, a netbook, a mobile phone, a smart phone, a personal digital assistant, or any other device capable of communicating with other devices by way of a network. ID component 232 stores at least temporarily a device identifier associated with the user device 230. Generally, the device identifier is a unique identifier. For example, the device identifier may be a Bluetooth beacon identification, a MAC address, and/or any computer readable identification protocol.

Transmitter 234 may be a wireless terminal that communicates location information. For example, the transmitter 234 may comprise a radio that transmits or receives radio communications over various wireless networks using wireless protocols, such as code division multiple access ("CDMA"), global system for mobiles ("GSM"), or time division multiple access ("TDMA"), as well as others. The radio communications may be a short-range connection, a long-range connection, or a combination of both a short-range and a long-range connections. When we refer to "short" and "long" types of connections, we do not mean to refer to the spatial relation between two devices. Instead, we are generally referring to short range and long range as different categories, or types, of connections. In one aspect, a short-range connection may include a radio-frequency identification (RFID) tag and an RFID tag reader. For instance, the RFID tag reader may capture the particular RFID tag scanned and any information associated with scanning, such as the time/date stamp, the particular radio-frequency scanned, the location of the RFID scanner, etc. In a second aspect, a short-range connection may include Bluetooth, Bluetooth LE, Zigbee (IEEE 802.15.4), 6LoWPAN, and the like. A long-range connection may include a connection using one or more of CDMA, GPRS, GSM, TDMA, 3G, 4G, 802.16 protocols, and such.

User device 240 may take on a variety of forms, such as a personal computer, a laptop computer, a tablet, a netbook, a mobile phone, a smart phone, a personal digital assistant, or any other device capable of communicating with other devices by way of a network. In one embodiment, user device 240 is a type of device described herein with respect to FIG. 1. Makers of illustrated user devices include, for example, Research in Motion, Creative Technologies Corp., Samsung, Apple, Nokia, Motorola, Microsoft, and the like. A user device 240 may comprise, for example, a display(s), a power source(s) (e.g., a battery), a data store(s), a speaker(s), memory, a buffer(s), and the like. In embodiments, user device 240 comprises a wireless or mobile device with which a wireless telecommunications network(s) can be utilized for communication (e.g., voice and/or data communication). ID component 242 stores at least temporarily a device identifier associated with the user device 230. Generally, the device identifier is a unique identifier. For example, the device identifier may be a Bluetooth beacon identification, a MAC address, and/or any computer readable identification protocol.

Location component 244 generally detects the location of user device 240. A user device may determine its own location based on: triangulation of cellular, WiFi, or similar signals; signals detected from GPS, GLONASS, Galileo, or similar satellite based systems; or any other suitable location determination system.

Figure 3:
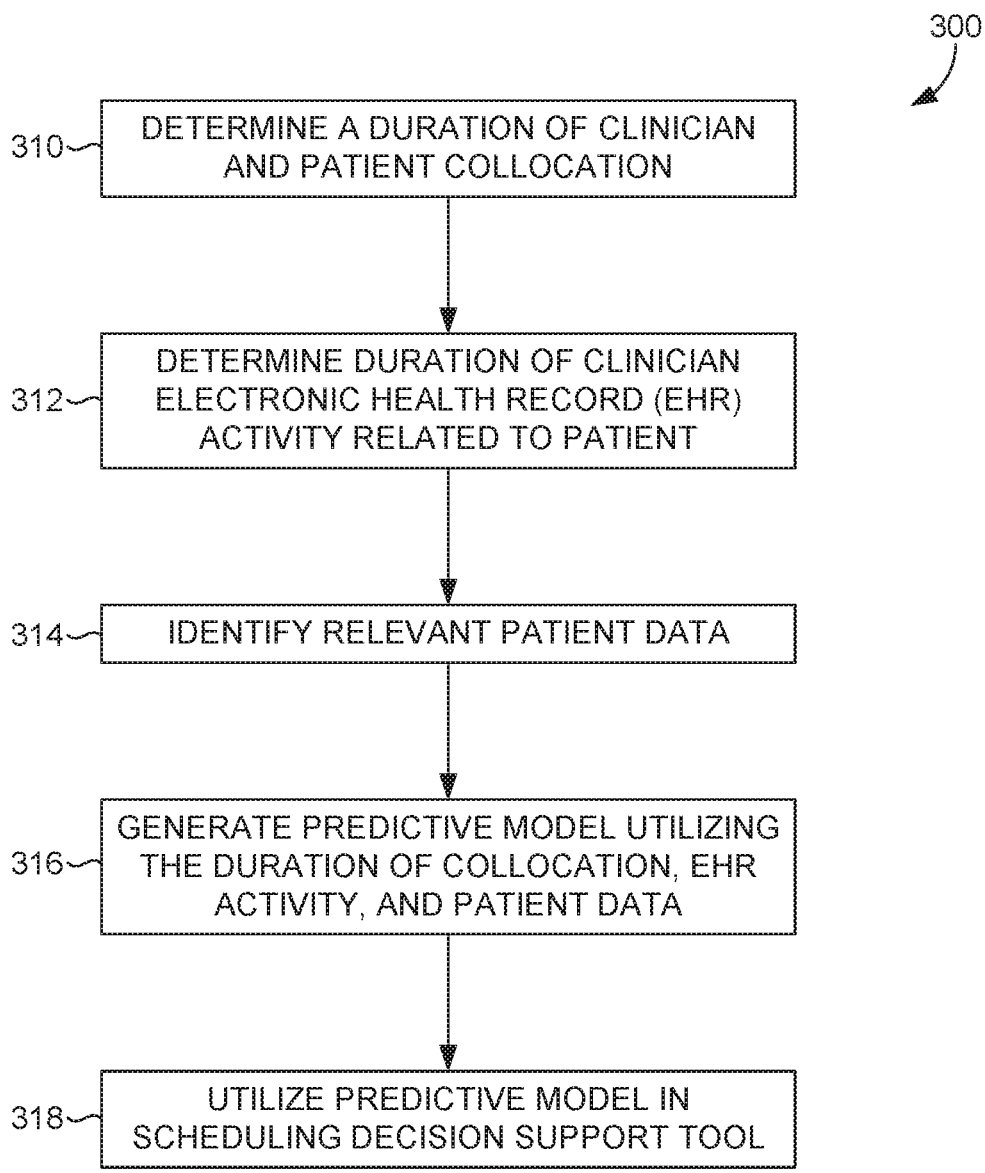
FIG. 3 depicts an exemplary method for generating a predictive model and facilitating scheduling decisions through an automated support tool, in accordance with an embodiment of the present invention.

Turning to FIG. 3, an exemplary method 300 for generating a predictive model and facilitating scheduling decisions through an automated support tool is depicted. Some embodiments of method 300 are suitable for implementation by system 200. Generally, method 300 comprises determining a duration of clinician and patient colocation, identifying relevant patient data, and generating a predictive model. Further, some embodiments of method 300 also include determining a duration of clinician electronic health record activity, training the predictive model, and/or utilizing the predictive model in a scheduling decision support tool. Some embodiments of method 300 include steps not explicitly depicted and/or include different, alternative, or additional steps. For instance, depending on the capabilities, configuration, or infrastructure of a specific hospital, clinic, health care provider, and/or health care facility method 300 may begin with the installation of one or more wireless receivers, such as wireless receiver 220. The installation may be permanent or temporary. Further, some embodiments of method 300 may also include associating wireless receivers, whether previously existing or newly installed, with specific locations in the hospital, clinic, health care facility, or the like. For instance, wireless receiver 1 may be assigned a location corresponding to clinic room 101, wireless receiver 2 may be assigned to clinic room 102, and so on. It will be understood by those skilled in the art that the preceding is merely an illustrative example, not meant to limit the scope of the embodiments described herein. For instance, wireless receivers may also be assigned to non-clinic rooms such as nurses' stations, lounges, office rooms, emergency rooms, and so on. Further, multiple wireless receivers may be assigned to a single room. For example, in a multi-occupant emergency room a receiver may be located at each patient treatment location and/or several pre-identified locations.

At block 310, a duration of clinician and patient colocation is determined. In some embodiments, determining that a clinician and a patient are colocated is based on multiple determinations. For instance, determining a clinician location for each clinician of the set of clinicians at multiple of time points. For another example, determining a patient location at multiple of time points for each patient of the set of patients In an embodiment the clinician-patient colocations are identified by correlations between the clinician location and corresponding time points, and the patient location and corresponding time points, thereby identifying a set of time points in which at least one clinician is colocated with a patient. In other words, a clinician's location is identified at a series of time points, a patient's location is identified at a series of time points, and where the clinician location and the patient location are determined to be similar at substantially similar time points the clinician and the patient are determined to be colocated. The duration of the colocation may then be calculated based on the first time point of clinician and patient colocation and the last point of clinician and patient colocation.

In some embodiments, the clinician's location is determined by determining the location of a user device, such as user device 230 and/or 240, associated with the clinician. For example, a clinician may carry a user device (230 and/or 240) for a period of time. The user device location may then be used as a proxy for the clinician location. In some embodiments of block 310 a user device location is determined by analyzing a set of device identifiers, signal strengths, corresponding time stamps, and wireless receiver identifiers. For instance, a user device, such as user device 230, may be configured to broadcast a device identifier as discussed in regards to FIG. 2. A wireless receiver, such as wireless receiver 220, may receive the device identifier; generate a time stamp corresponding to the time at which the receiver received the broadcast; and generate a numerical representation of the signal strength associated with the device identifier broadcast. The wireless receiver may communicate this data and a wireless receiver identifier, directly or indirectly, to a time analysis engine, such as time analysis engine 210.

However, it will be readily apparent to those skilled in the art that in embodiments of method 300 implemented in a system with a plurality of wireless receivers (such as wireless receiver 220), it is possible that multiple wireless receivers will detect the device identifier broadcast by a specific user device (such as user device 230) at any given time. This is, at least partially because, the broadcast signal may bounce off of surfaces, penetrate unshielded walls, and/or otherwise leak beyond the physical area immediately around the user device. As such, a device location may be determined from the possible locations associated with the wireless receivers that detect the broadcast signal at the same (or substantially the same) time by processing the raw signal strength data and comparing the results. In other words, the user device may be determined to be located at the location of the wireless receiver with the highest signal strength after processing the raw signal strength data. In some embodiments, the processing of the raw signal strength data may comprise determining the geometric, arithmetic, and/or weighted arithmetic mean of the signal strengths detected by the wireless receivers corresponding to a predetermined number of the previous and/or subsequent device identifier broadcasts. Additionally, and/or alternatively, processing the raw signal strength data may comprise a sliding (rolling) window smoothing of the signal strengths. For example, in an embodiment processing the signal strength comprises calculating the mean signal strength for each wireless receiver in a 180 second segment. In some embodiments, the processing includes flittering the smoothed signal strengths to discard any signals below a received signal strength indication (RSSI) threshold. For example, the smoothed signal strengths for each receiver are filtered by applying a −80 dB RSSI threshold. Smoothed signal strengths that are below the threshold may be discarded. In some embodiments, the processing includes comparing the smoothed and filtered signal strengths and determining that the location of the clinician is the location of the wireless receiver with the strongest (e.g. largest, highest in value) signal strength. It will be understood by those skilled in the art that the preceding examples are intended as illustrative and as such not intended to limit the scope of the embodiments described herein.

In some embodiments, the clinician's location is determined by the user device, such as user device 240. For instance, as discussed in regards to FIG. 2, a user device may determine its own location based on: triangulation of cellular, WiFi, or similar signals; signals detected from GPS, GLONASS, Galileo, BeiDou-2, or similar satellite based systems; or any other suitable location determination system.

A patient's location at various time points may be determined in a variety of ways. In some embodiments metadata associated with the patient data is used to determine the location of a patient. For example, when the patient arrives for an appointment an indication may be made in the patient's electronic health record that the patient has arrived for their schedule appointment. The metadata associated with this entry may indicate the time the entry was made and/or the remote computer, such as remote computer 108, at which the entry was made. Where both the entry time and the identity of the remote computer are indicated by the metadata patient's location may be determined to be the location of the remote computer or the area proximate to the location from the associated time, $T_x$, until the next time indicated by the metadata. Where only the entry time associated with the patient check-in is captured in the metadata, the location of the patient may be assumed to be in a location corresponding to the waiting room and/or in any other predefined location. Further, during check-in and/or registration the patient may be assigned a specific room, treatment area, and/or bed.

In some embodiments, the patient location is determined to have changed from the initial "waiting room" location to the assigned room at $T_y$, in response to the occurrence of at least one of a first set of predetermined actions within the patient's EHR. For instance, the first set of predetermined action may comprise the first occurrence of a clinician opening the patient's EHR, on a remote computer, after the patient has completed check-in and/or registration. Additionally, and/or alternatively, the first set of predetermined actions may comprise the entry of the first clinical event, vital signs, family history, social history, medical procedure history, general medical history, medication history, or any other indication within the patient's electronic health record indicative of an initial interaction between the patient and a clinician. Thus, for example, a given patient may be determined to be in the waiting room or other predefined location from $T_x$ until $T_y$.

Further in some embodiments, the patient location is determined to be the assigned room and/or bed from $T_y$ until $T_z$. $T_z$ may be detected in response to the occurrence of at least one of a second set of predetermined actions indicative of patient check-out within the patient's EHR. For example, entry and/or scheduling of new appointment, an indication that the patient has paid an applicable co-pay and/or other bill, an indication that a medication prescription and/or patient-clinician follow-up instructions has been distributed to the patient, and similar actions within the patient's EHR may indicate that the current appointment is concluding/concluded and the patient may be determined to have moved from the assigned room. Thus, for example, a given patient may be determined to be located in the room and/or bed assigned in the patient's EHR from $T_y$ until $T_z$.

In some embodiments, the patient location may be determined by metadata associated with the scanning of a machine readable indicator (barcode, RFID, and the like) assigned to the patient by a scanning device associated with a remote computer, such as remote computer 108, at a known location. In some embodiments, a patient may be given a user device, such as user device 230 or 240, that is temporarily associated with the patient. As such, in some embodiments, determining the patient location is accomplished in a substantially similar way to the determination of the clinician location based on the location of a user device associated with the clinician.

The clinician locations and corresponding time stamps are compared to the patient locations and corresponding time stamps. Where the clinician location and the patient location correspond to each other at the same time (or substantially similar time) the clinician and patient are determined to be colocated. At block 312, a duration of clinician activity in the patient's EHR is determined. Generally, the duration of clinician activity is the length of time between which a clinician opens the patient's EHR and closes the patient's EHR. In some embodiments, the duration of clinician activity is further segmented into a duration of EHR activity while colocated with the patient and a duration of EHR activity while not colocated with the patient.

At block 314, identify relevant patient data for the predictive model. Generally, by identifying a set of available variables from the data provided to or otherwise accessible by to a time analysis engine, such as time analysis engine 210, a predictive model may be generated that models the patient appointments while accounting for any variability unique to the hospital, clinic, hospital network, etc. and reducing the computation burden required to model the appointments. For example, in an embodiment, identification of relevant patient data may include building regression model(s) to identify variables that are correlated to clinician work effort (e.g., clinician-patient colocation and/or duration of EHR activity). In an embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including, in an embodiment, leaps package, may be utilized for identifying the subset of patient data which is relevant for the predictive model. The leaps package, and other similar packages, may be used to perform an exhaustive search for the best subsets of the variables in patient data for predicting clinician work effort in linear regression. For example, patient data including appointment type (such as RT1, RT2, and the like), reason for appointment (such as a 4 month well child check, child has cough, child wheezing, and so on), the name of the patient's physician, demographic patient information, the number of active patient complaints, the number and recency of emergency and urgent care visits, documented medications, the patients primary language, and the position of the appointment in the day (such as the first on appointment of the day, second on appointment of the day, third on appointment of the day, and so on) may be identified as having a corollary relationship to the duration of the clinician-patient colocation. In other words, one or more sets of categories of patient data (e.g., appointment type, reason for appointment, demographic patient information, and so on) may be identified from all of the categories of patient data in an EHR system as having an influence on clinician work effort. In some embodiments, one, more than one, or a plurality of sets of patient data categories may be identified as relevant patient data. At block 316, at least one predictive model is generated. Generally, the predictive model is generated so that the model approximates the activity being modeled. For example, an appointment can be modeled as three discrete events, patient arrival, a clinician-patient interaction, patient departure. For another example, an appointment can be modeled as five discrete events: patient arrival, a first clinician-patient interaction (for instance a nurse-patient interaction), a second clinician-patient interaction (for instance a physician-patient interaction), clinician-EHR activity, and patient departure. Further, in an embodiment the predictive model is generated to model patient appointments by representing discrete events during the appointment where the duration of at least one of the discrete events is a function of the patient data identified as having a statistically significant correlation to duration of clinician-patient colocation identified in block 314. For example, a predictive model may be generated that represents a first discrete event (e.g. patient arrival) as creation of an entity (patient) with a set of attributes (variables identified as statistically correlated to the variability of the duration of clinician-patient colocation, such as the relevant patient data identified at block 314). Each attribute can have a defined set of possible values that may be randomly or pseudo-randomly assigned to the entity. For instance, the model may create a patient with the number of active complaints with a first randomly assigned value, the number and recency of emergency and urgent care visits with a second randomly assigned value, documented medications with a third randomly assigned value, and so on. In an embodiment, the defined set of possible attribute values may be based on the values observed in the patient data actually used to identify the attributes.

For another example, a predictive model may be a Markov process model, such as a Markov chain, of patient data, such as patient data 202. In an embodiment, patient data comprising appointment type (such as RT1, RT2, and the like), reason for appointment (such as a 4 month well child check, child has cough, child wheezing, and so on), the name of the patient's physician, demographic patient information, the number of active patient complaints, the number and recency of emergency and urgent care visits, documented medications, the patients primary language, and the position of the appointment in the day (such as the first on appointment of the day, second on appointment of the day, third on appointment of the day, and so on) are identified as Markovian relationship to the duration of the clinician-patient colocation. However, it will be understood by those skilled in the art that analysis of a particular set of patients and clinicians may identify the same, similar, and/or different categories of patient data as relevant to the predictive model because of the categories statistical correlation to differences in the duration of the clinician-patient colocation.

At block 318, the predictive model may be utilized in a scheduling decision support tool. Generally, the model is utilized to identify a suggested patient appointment duration and/or appointment slot. The model may be incorporated into the background operations of a scheduling component of the electronic health record system for the hospital, clinic, hospital network, and/or the like. When an appointment request is made for a particular patient, the scheduling decision support tool may be activated. In some embodiments, the scheduling decision support tool may access patient data associated with the particular patient, identify the patient data that corresponds to the variables of the generated predictive model, and use the corresponding patient data as inputs into the predictive model.

Further, in an embodiment, the decision support tool may access the currently scheduled appointments for one or more clinicians associated with the appointment request. Based on the currently scheduled appointments, the decision support tool may determine a set of available appointment durations and/or a set of available appointment slots. The decision support tool may limit the operational parameters of the predictive model such that only the set of available appointment durations and/or the set of available appointment slots are permitted as recommended appointment durations and/or slots.

Figure 4:
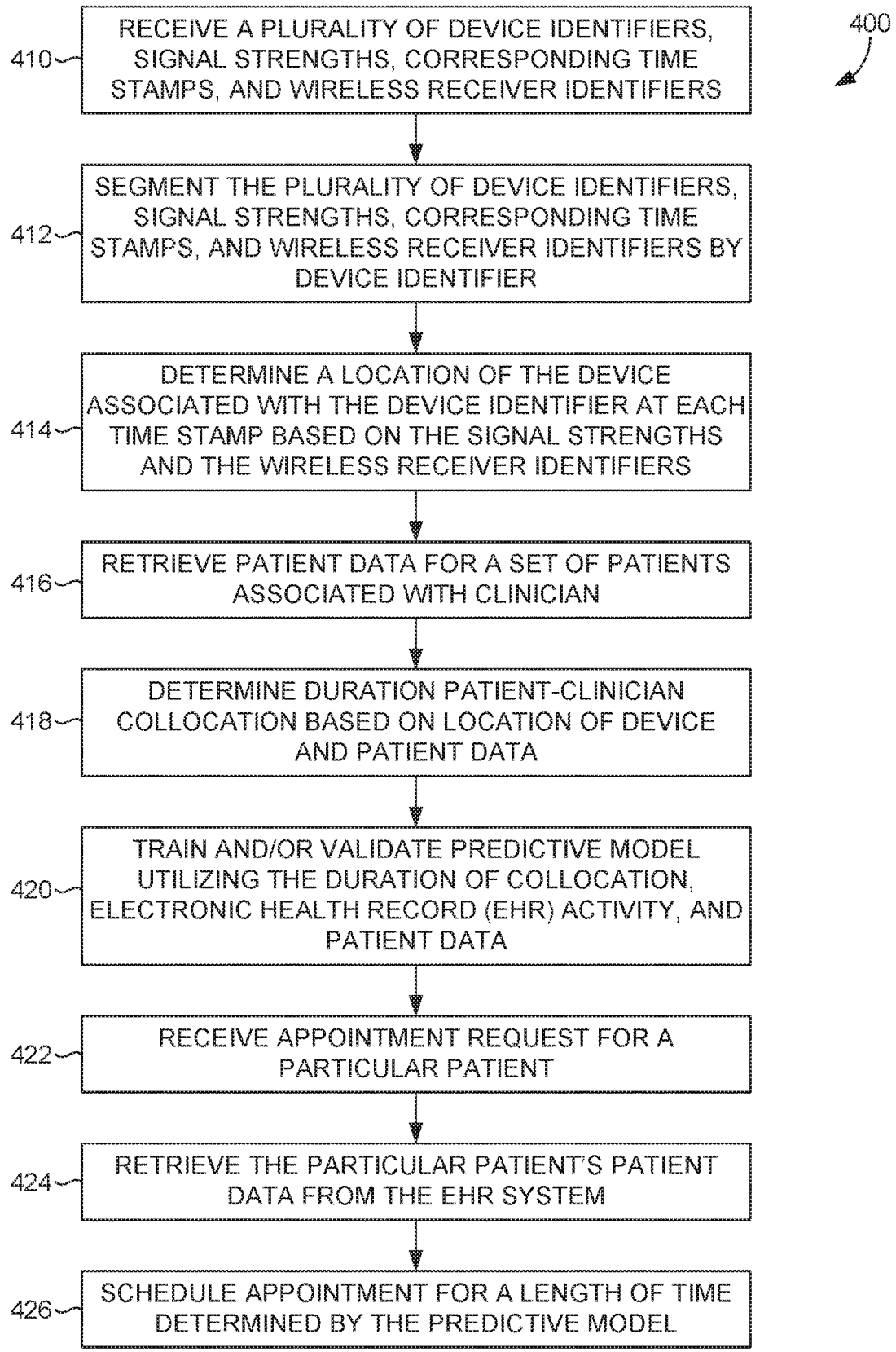
FIG. 4 depicts another exemplary method for generating a predictive model and facilitating scheduling decisions through an automated support tool, in accordance with an embodiment of the present invention.

Turning to FIG. 4, an exemplary method 400 for generating a predictive model and facilitating scheduling decisions through an automated support tool is depicted. Generally, method 400 comprises receiving a data from a plurality of user device, segmenting the data by user device, based on the segmented data determining a location of each device, and retrieving patient data associated with a clinician. Based on the patient data and the device locations, duration of clinician patient colocation is determined. Based on at least the duration of the clinician-patient colocation, a predictive model is trained; and, in response to receiving a particular patient appointment request the predictive model is utilized to assist in scheduling the appointment. Further, some embodiments of method 400 also include determining a duration of clinician electronic health record activity. The clinicians EHR activity may also be used to train the predictive model. Some embodiments of method 400 are suitable for use within system 200.

At block 410, a plurality of device identifiers, signal strengths, corresponding time stamps, and wireless receiver identifiers are received. In some embodiments of block 410, the device identifiers, signal strengths, corresponding time stamps, and wireless receiver identifiers are received directly and/or indirectly by a time analysis engine, such as time analysis engine 220. The device identifiers comprise a unique identifier that corresponds to and is broadcast by a specific user device, such as user device 230 and/or 240. Some embodiments of block 410 further comprise, receiving EHR activity data for a clinician. The EHR data may represent the total amount of time spent in the one or more EHRs by each clinician and a location or set of locations at which the clinician accessed the EHR.

At block 412, the device identifiers, signal strengths, corresponding time stamps, and wireless receiver identifiers are segmented to a per-device identifier data level such that the data illustrates the wireless receiver identifiers, signal strengths, and corresponding time stamps. Some embodiments of block 412 further comprise identifying a particular clinician based on an association between the device identifier and the clinician. At block 414, a location of the device associated with the device identifier at each time stamp is determined based on the signal strengths and the wireless receiver identifiers. For instance, determining the location of the device may comprise calculating the geometric, arithmetic, and/or weighted arithmetic mean of the raw signal strengths for a predetermined number of previous and/or subsequent time stamps reported by each wireless receiver. The geometric, arithmetic, and/or weighted arithmetic means may be compared. The value corresponding to the strongest signal (highest value) may be identified as the wireless receiver location for the time stamp and the location of the device may be determined to correspond to the wireless receiver location.

At block 416, patient data for a set of patients associated with a clinician is retrieved. Generally, the set of patients associated with the clinician are those patients which the clinician was scheduled to see for an appointment and who actually arrived for the appointment between the first time stamp for a device identifier and the last time stamp for a device identifier. In some embodiments of block 416, the clinician's appointment scheduling information is used to identify candidate patients. Patient data 202 corresponding to each candidate patient is identified in a communicatively coupled EHR system. Patient check-in information is detected and a determination is made whether the patient was seen by the clinician.

At block 418, a duration of patient-clinician colocation is determined based on location of device and patient data. The clinician locations and corresponding time stamps are compared to a patient room assignment and corresponding time stamp in the patient's patient data 202. Where the clinician location and the patient room assignment correspond with each other at an overlapping time (or substantially similar time) the clinician and patient are determined to be colocated. At block 420, utilizing the duration of patient-clinician colocation, EHR activity, and patient data a predictive model is trained and/or validated. Generally, the predictive model is comprises a set of variables, attributes, and events. The model may be trained and/or validated by providing input data corresponding to the entities, attributes, and events in the model. For example, patient data corresponding to the variables of the model from the EHR of patients actually seen by the clinician may be provided as inputs for the set of attributes. In other words, the variables of the predictive model may be identified as corresponding to categories of patient data in the EHR system of the health care provider. The patient data for the patients of the clinician(s) the predictive model is simulating may be collected as a pool of potential attributes for the variables of the predictive model. For another example a chronologically sequenced order of patient check-in and corresponding duration, patient-clinician colocation and corresponding duration, and patient check-out may be identified and provided as inputs for the set of events.

At block 422, a request for an appointment is received for a particular patient. Generally, the appointment request may be made by a clinician, patient, or person responsible for the care of the patient (e.g. a parent). The request may indicate a preferred time or window of time, a reason for the appointment (yearly check-up, persistent cough, post-surgery follow up, etc.), and the identity of the patient. Further, a scheduling component of the electronic health record system may activate a scheduling decision support tool. At block 424, the particular patient's patient data from the EHR system is retrieved. Additionally, the variables of the predictive model are identified and the corresponding data within the patient data of the patient's EHR is input into the model. Further, in an embodiment, the decision support tool may access the currently scheduled appointments for one or more clinicians associated with the appointment request. Based on the currently scheduled appointments, the decision support tool may determine a set of available appointment durations and/or a set of available appointment slots. The decision support tool may limit the operational parameters of the predictive model such that only the set of available appointment durations and/or the set of available appointment slots are permitted as recommended appointment durations and/or slots. At block 426, a recommended duration and/or appointment timeslot for the requested appointment is determined by the predictive model and presented as output from the model.

Figure 5B:
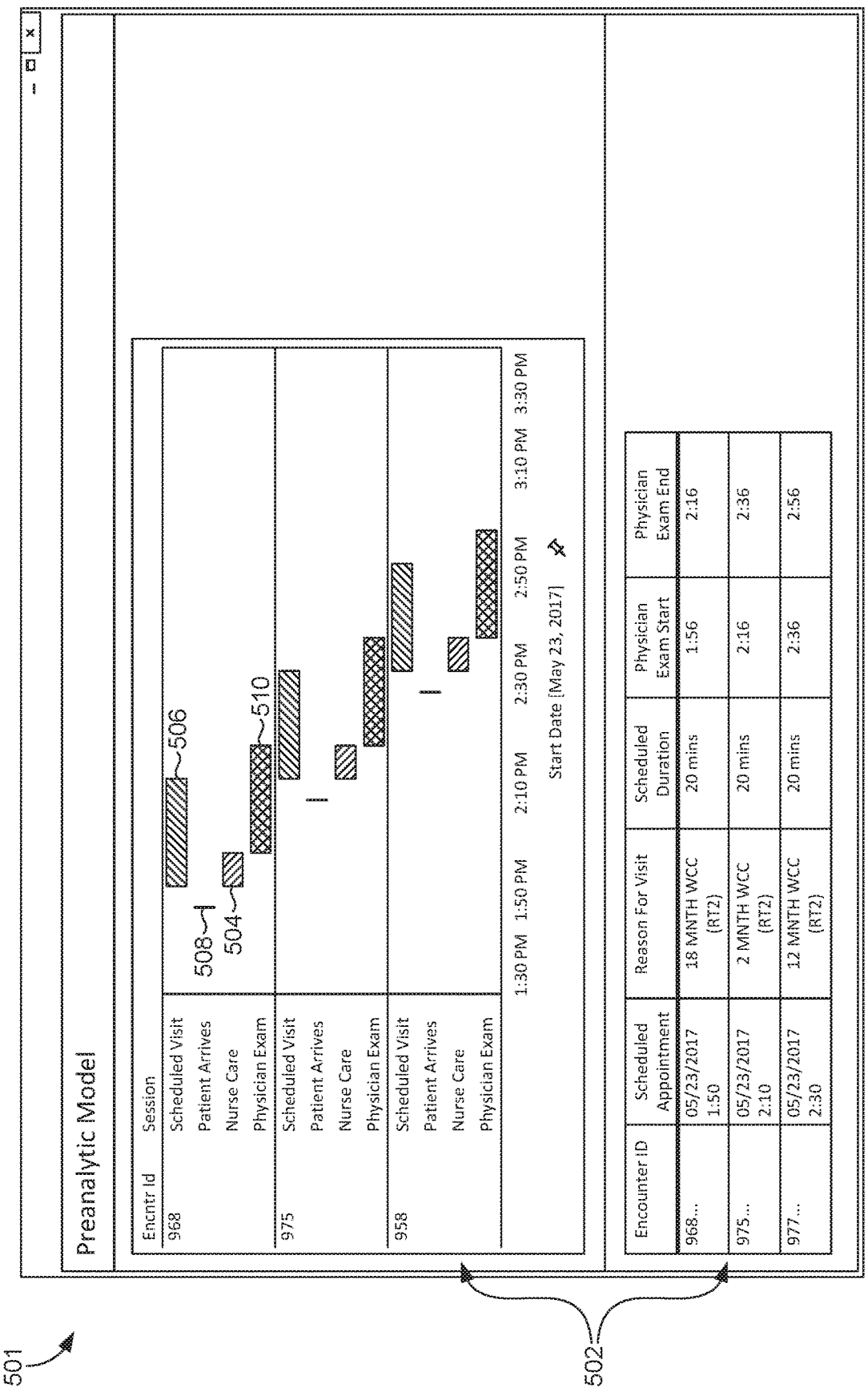

FIGS. 5A and 5B generally depict a portion of an exemplary schedule for a clinician stored in an EHR system received by an actually reduced to practice embodiment of a time analysis engine, such as time analysis engine 210. As depicted, this example reflects the clinician's schedule 500 on May 23, 2017 and depicts a deidentified portion of scheduled appointments for the clinician from 1:50 pm through 4:10 pm; the reason for each appointment (for example an 18 month well child care appointment, a 2 month well child care appointment, a patient complaint of wheezing, and so on); an appointment type (RT 2 or RT 1); and a scheduled duration (20 minutes or 10 minutes). A subset of the clinician's schedule 502 is depicted in a graphical user interface (GUI) 501 for interacting with a time analysis engine. As depicted, the GUI 501 may display the overall scheduled times 506. Further, appointment scheduling information may be used to identify the expected time and/or duration constituent parts of the scheduled appointment. For example, an expected patient arrival time 508 and duration, an expected first clinician-patient interaction 504 and a duration, and an expected second clinician-patient interaction 506 may be identified by the time analysis engine 210 and presented in a GUI, such as GUI 501.

Figure 6A:
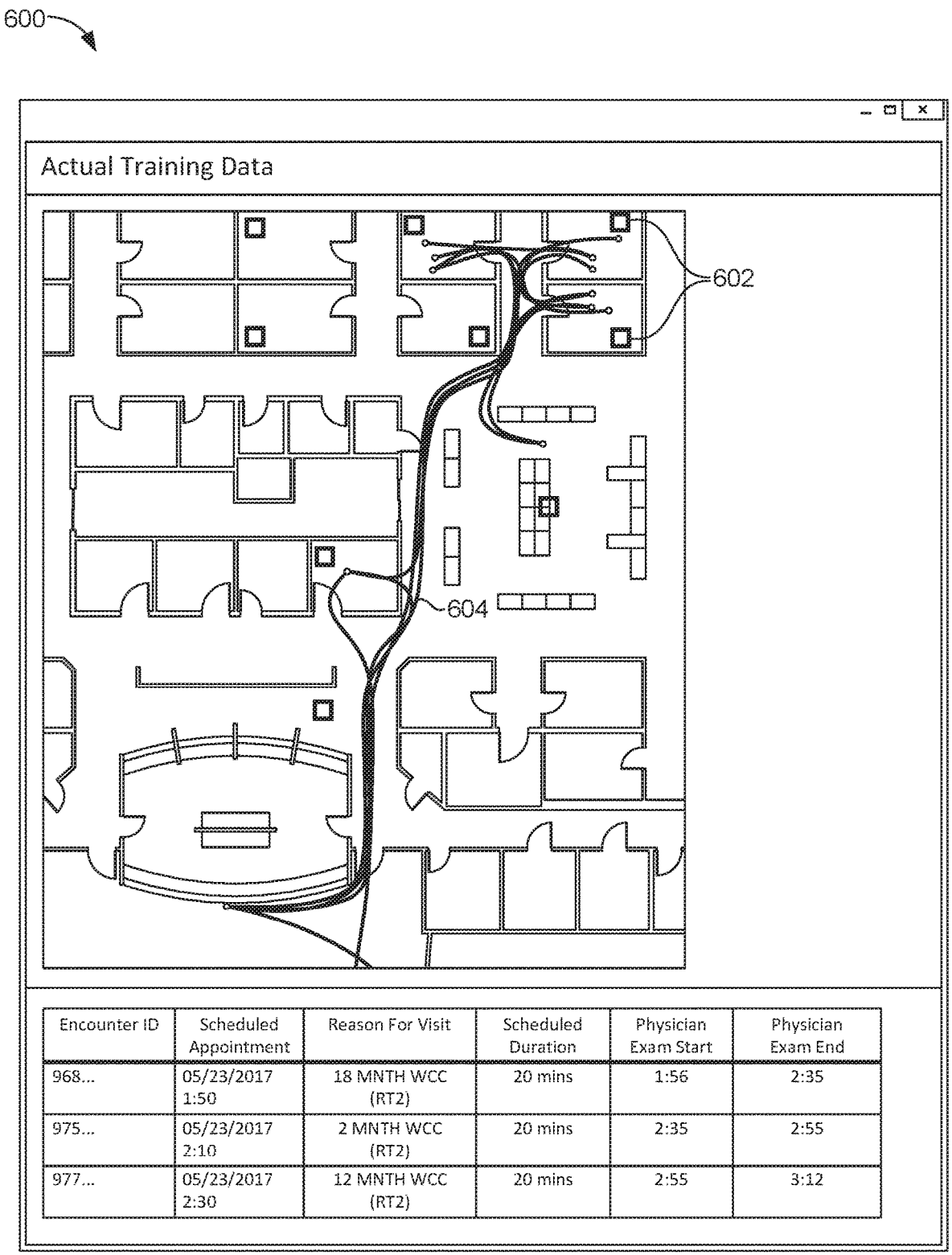
FIGS. 6A and 6B generally depict a portion of clinician location data summary, in accordance with an embodiment of the present invention.
Figure 6B:
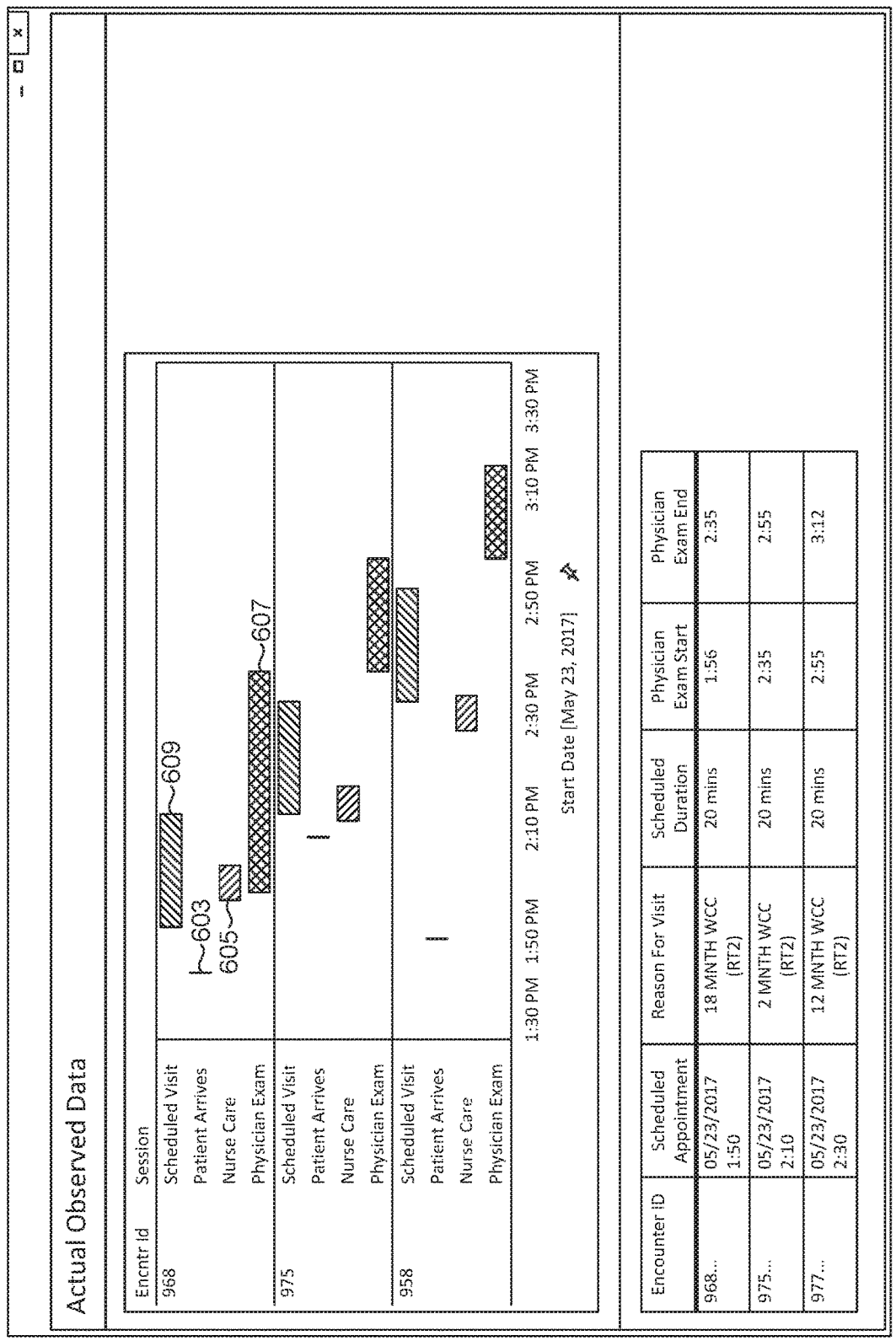

FIGS. 6A and 6B generally depict a portion of clinician location data generated by an embodiment of a time analysis engine, such as time analysis engine 210. As illustrated, GUI 600 depicts a graphical version of the clinician's location 604 at a plurality of time points. In an embodiment, the clinician's location may be displayed in GUI 600 at any single time point, at two or more time points, all time points, and/or in chorological order. Further, GUI 600 may depict the location(s) 602 of wireless receivers, such as wireless receiver 220. As illustrated, GUI 601 depicts the actually observed time and/or duration of the constituent parts of the scheduled appointment(s), based on the analysis of a time analysis engine, such as time analysis engine 210. For example, the patient's actual arrival time 603 and check-in duration; the actual first clinician-patient interaction 605 and a duration; and, the actual second clinician-patient interaction 607 may be identified by the time analysis engine 210 and presented in a GUI, such as GUI 601. Additionally, GUI 601 may depict the scheduled appointment time and/or duration 609.

FIG. 7 depicts a graphical representation of a portion of the output from a time analysis engine, such as time analysis engine 210. The illustrated output depicts the scheduled duration of appointment types RT1 and RT2 as compared to the actually observed mean duration for appointment types RT1 and RT2. Further, the observed mean duration may be presented based on individual clinicians (Dr. #1 and Dr. #2 for example) and/or combinations of observed clinicians (for example Overall).

Figure 8:
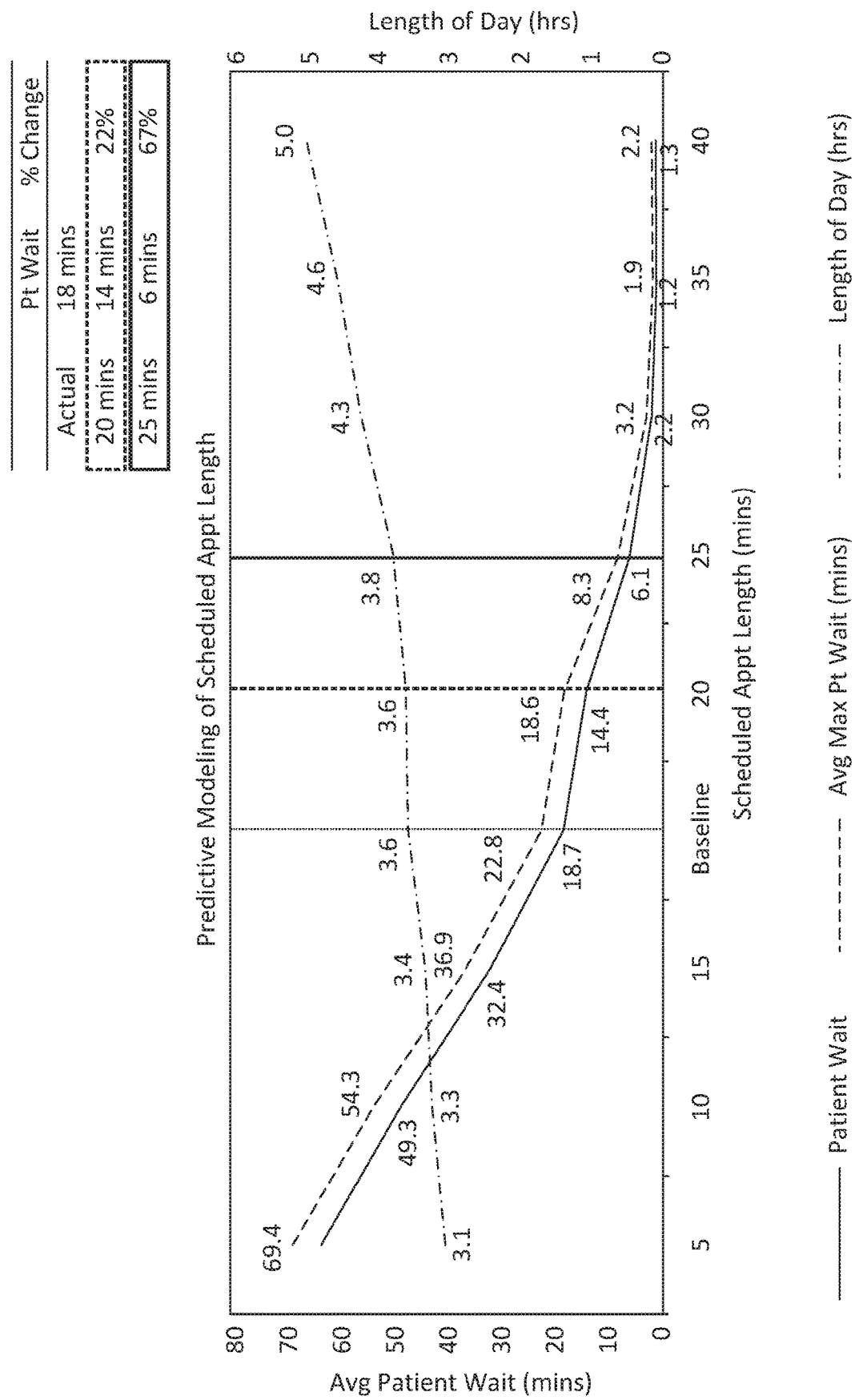
FIG. 8 depicts a dimensionally reduced representation of a simulation of a predictive model.

FIG. 8 depicts a graphical representation provided by of a predictive model. To ease visualization of the predictive model the dimensionality has been reduced. It will be understood by those skilled in the art that this is intended merely as illustrative example and that the reduced dimensionality is not intended to limit the scope the embodiments described herein. The graphical representation includes the scheduled appointment length prior to implementation of the predictive model (baseline) and a predictive model's simulated results of modifying an appointment length to various durations.

Figure 9:
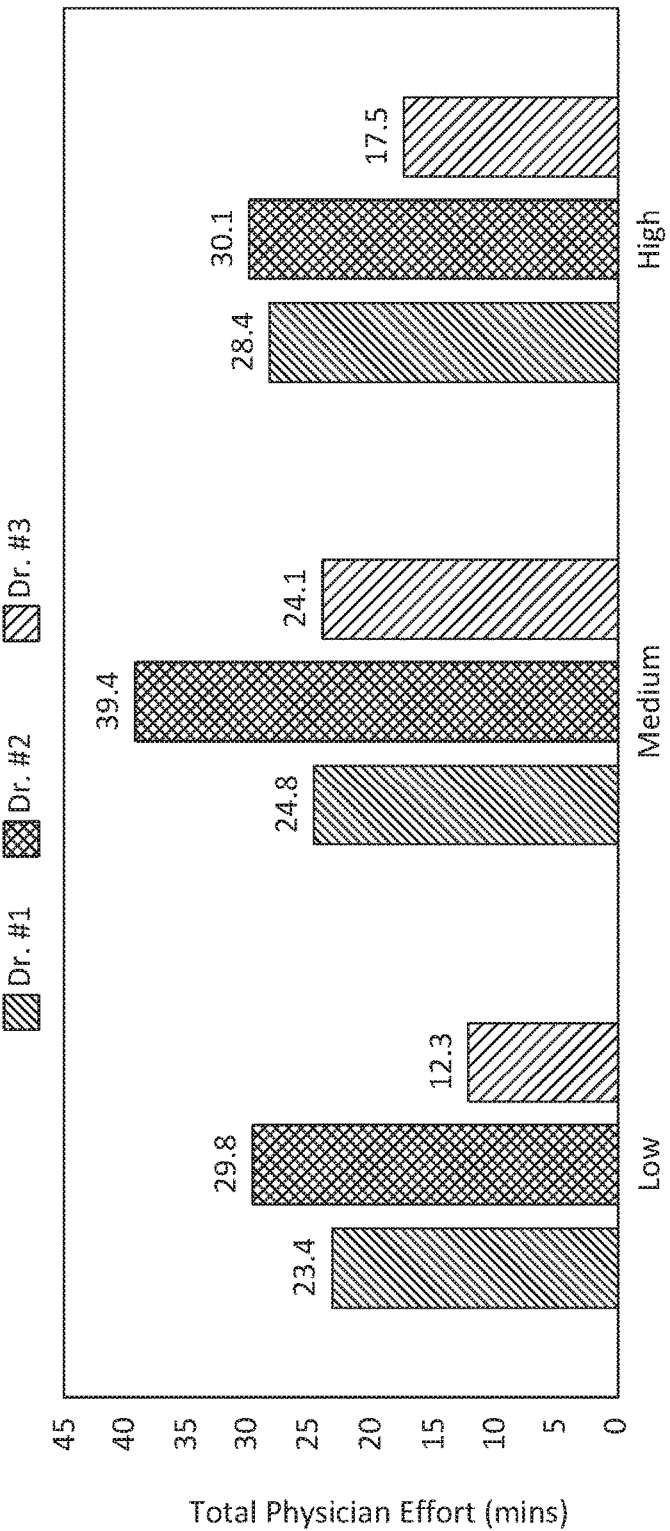
FIG. 9 depicts a per-clinician analysis summary, in accordance with an embodiment of the present invention.
Figure 10:
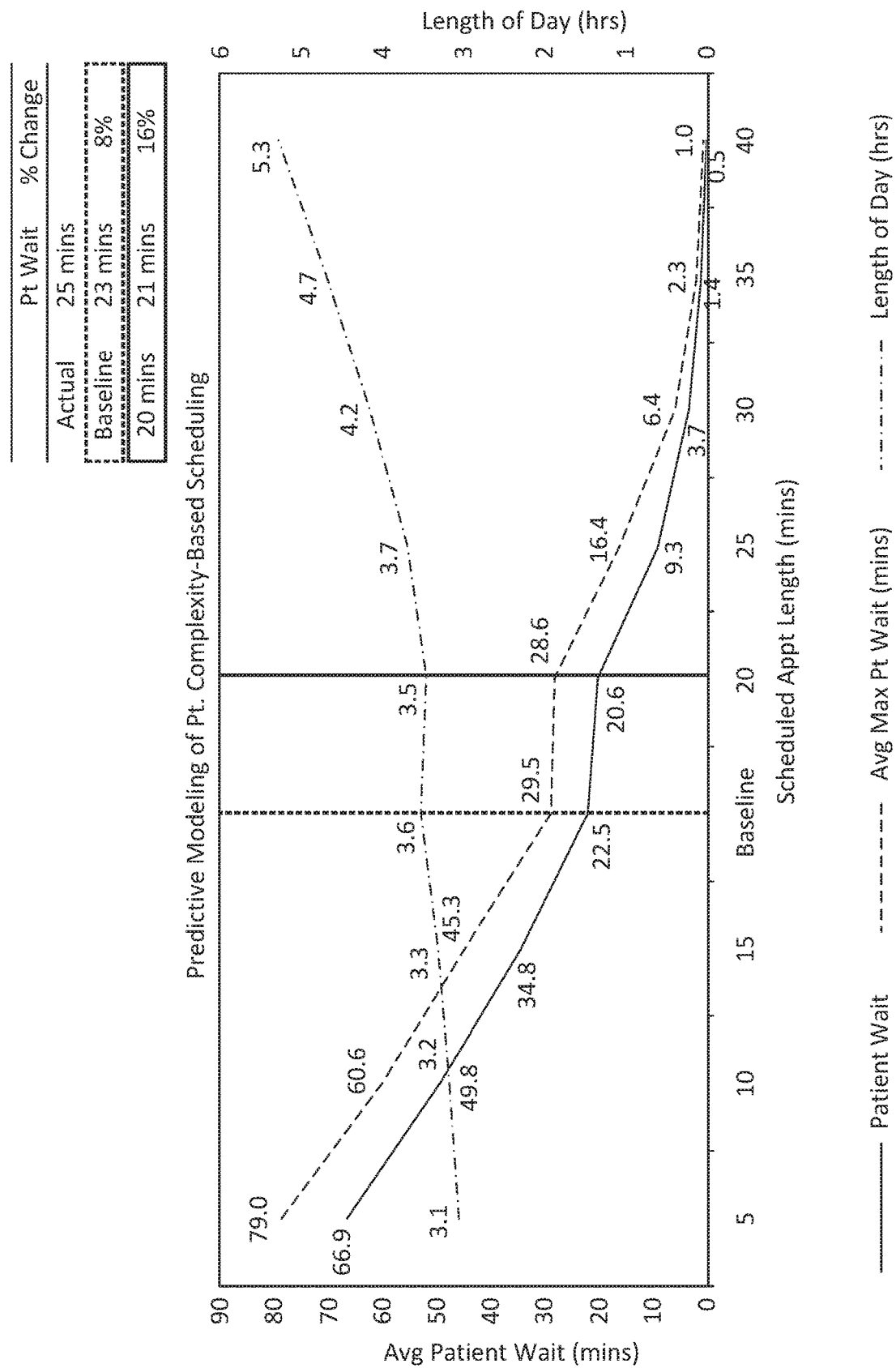
FIG. 10 depicts another dimensionally reduced representation of a simulation of a predictive model, in accordance with an embodiment of the present invention.

FIGS. 9 and 10 generally depict a portion of the output of a trained predictive model and the predictive analysis of a trained predictive model. In this embodiment, analysis of the patient data received by the time analysis engine identified a set of relevant categories of patient data. The three cohorts of patients (High, medium, and low complexity) were identified based on the relevant categories of patient data. Further, FIG. 10 generally depicts a portion of output from the predictive model actually reduced to practice which was controlled to demonstrate the effect of assigning appointment slots based on model determined patient complexity.

The phrase "in one embodiment" or "in an embodiment" is used repeatedly. The phrase generally does not refer to the same embodiment; however, it may. The terms "comprising," "having," and "including" are synonymous, unless the context dictates otherwise. The phrase "A/B" means "A or B." The phrase "A and/or B" means "(A), (B), or (A and B)." The phrase "at least one of A, B and C" means "(A), (B), (C), (A and B), (A and C), (B and C) or (A, B and C)."

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

What is claimed is:

1. A system comprising:
a wireless communication device for communicating a device identifier;
a plurality of wireless receivers, wherein each of the plurality of wireless receivers is configured to receive the device identifier communicated by the wireless communication device, determine a signal strength, and generate a time stamp associated with the receipt of the device identifier;
one or more processors; and
computer readable instructions that cause the one or more processors to perform operations comprising:
receiving the device identifier, the signal strengths, and the associated time stamp from a set of the plurality of wireless receivers;
determining a smoothed signal strength for the device identifier based on the signal strengths received by each wireless receiver of the set of wireless receivers;
based on the smoothed signal strength and the associated time stamp, determining a location of the wireless communication device at a first time;
based on the location of the wireless communication device, determine that a provider associated with the wireless communication device is at the determined location;
retrieving appointment data associated with a patient, the appointment data comprising patient check-in time, patient room assignment, patient roomed time, and patient check-out time;
based on the patient roomed time, the patient check-out time, and the patient room assignment determining that the patient was located at the location corresponding to the room assignment for time points between the patient roomed time and the patient check-out time;
based on the time stamp, the determined location, and the room assignment determine that the provider and the patient are colocated;
accessing patient data for the patient;
responsive to the determination that the provider and the patient are colocated providing to a tuned predictive model the provider's determined location, the appointment data, and the patient data corresponding to input variables of the predictive model, the predictive model determined based on a plurality of discrete events representative of a clinical appointment including at least one event with a duration variably dependent on patient data; and
generating an available clinic appointment window for a particular patient with a duration variably dependent based on output of the tuned predictive model.

2. The system of claim 1, wherein the system further comprises a plurality of wireless communication devices, wherein the device identifier is different for each of the plurality of wireless communication devices.

3. The system of claim 1, wherein the system further comprises an electronic health record system for storing medical information for a plurality of patients.

4. The system of claim 3, wherein the system further comprises:
a plurality of remote user devices for accessing the electronic health record system; and
the computer readable instructions further cause the one or more processors to perform operations comprising:
identifying a first amount of time the provider accessed an electronic health record associated with the patient while the provider was colocated with the patient; and identifying a second amount of time the provider accessed the electronic health record associated with the patient while not colocated with the patient.

5. One or more non-transitory computer storage media having computer-executable instructions embodied thereon that, when executed, facilitate a method of time data analysis, the method comprising:

receiving a plurality of device identifiers, signal strengths, corresponding time stamps, and wireless receiver identifiers from a set of wireless receivers for receiving device identifiers broadcast by a set of devices, each device of the set of devices associated with a health care clinician of a plurality of clinicians;

determining a smoothed signal strength for each of the plurality of device identifiers based on the signal strengths received by each wireless receiver of the plurality wireless receivers;

segmenting the plurality of device identifiers, smoothed signal strengths, corresponding time stamps, and wireless receiver identifiers by device identifier thereby generating a per-device set of data for each device identifier comprising a plurality of signal strengths, corresponding time stamps, and wireless receiver identifiers;

generating a clinician location data set comprising a plurality of time stamped locations for each per-device set of data based on the smoothed signal strengths, the time stamps, and the wireless receiver identifiers;

retrieving appointment data associated with a plurality of patients, the appointment data comprising patient check-in time, patient room assignment, patient roomed time, and patient check-out time for each appointment of each patient of the plurality of patients;

generating time data including an amount of time each patient of the plurality of patients and a corresponding health care clinician of the plurality of clinicians were colocated based on the clinician location data set and the appointment data;

receiving patient data for the plurality of patients;

tuning a predictive model by supplying the predictive model the clinician location data, the appointment data, time data, and the patient data corresponding to input variables in the predictive model, the predictive model comprising a plurality of discrete events representative of a clinical appointment including at least one event with a duration variably dependent on patient data;

receiving a clinic appointment request for a particular patient, the appointment request corresponding to an appointment that is yet to occur;

in response to receiving the clinic appointment request, generating an expected duration for each of the plurality of discrete events utilizing a set of patient data associated with the particular patient as input variables for the tuned predictive model, wherein the set of patient data correspond to the input variables of the predictive model; and responsive to generation of an expected duration, generating the appointment for the particular patient corresponding to the clinical appointment request, the clinical appointment having a duration based on the generated expected duration of the at least one event with the duration variably dependent on patient data.

6. The computer storage media of claim 5, wherein determining a total amount of time the set of patients and the set of clinicians were collocated comprises:

determining a clinician location for each health care clinician of the plurality of clinicians at a plurality of time points;

determining a patient location at a set of the plurality of time points for each patient of the plurality of patients; and identifying correlations between the clinician location and corresponding time points, and the patient location and corresponding time points, thereby identifying a set of time points in which at least one clinician is colocated with a patient.

7. The computer storage media of claim 6, wherein determining the patient location further comprises:

receiving appointment data associated with the patient, the appointment data comprising patient check-in time, patient room assignment, patient roomed time, and patient check-out time; and based on the patient roomed time, the patient check-out time, and the patient room assignment determining that the patient was located at the location corresponding to the room assignment for the time points between the patient roomed time and the patient check-out time.

8. The computer storage media of claim 5, wherein the time data further comprises:

a first amount of time the plurality of clinicians accessed an electronic medical record associated with a patient of the plurality of patients while collocated with the patient; and a second amount of time the plurality of clinicians accessed the electronic medical record associated with the patient while not colocated with the patient.

9. The computer storage media of claim 5, wherein the input variables in the predictive model further comprise at least one of:

an appointment type;
a scheduled appointment duration;
a reason for visit;
a medication history;
a clinician identifier or name;
an indication of the patient's gender;
a weight associated with the patient;
a numerical indication of patient reported active problems;
an indication of emergency room or urgent care visits;
an indication of the patient's primary language; or
a representation of a chronologic position of the appointment.

10. The computer storage media of claim 5, wherein utilizing the tuned predicative model comprises:

receiving a set of available appointment durations or a set of available appointment slots;

receiving patient data for the particular patient corresponding to the input variables of the predictive model; and providing the predictive model the set of available appointment durations or the set of available appointment slots, and the patient data for the particular patient as inputs.

11. The computer storage media of claim 5, wherein the new appointment request comprises a preferred time, a reason for the appointment, or the identity of the patient.

12. The computer storage media of claim 5, wherein the input variables are determined by identifying Markov relationships between patient data and variations in patient appointments, variations in the duration of clinician-patient colocation, or variations in scheduled duration and actual duration.

13. A computer implemented method for using broadcast identifiers to predictively generate optimized scheduling, the method comprising:
  receiving a plurality of device identifiers, signal strengths, corresponding time stamps, and wireless receiver identifiers from a set of wireless receivers for receiving device identifiers broadcast by a set of devices, each device of the set of devices associated with a health care clinician of a plurality of clinicians;
  segmenting the plurality of device identifiers, signal strengths, corresponding time stamps, and wireless receiver identifiers by device identifier thereby generating a per-device set of data for each device identifier comprising a plurality of signal strengths, corresponding time stamps, and wireless receiver identifiers;
  determining, for each per-device set of data, a location of the device associated with the device identifier at each time stamp based on the signal strengths and the wireless receiver identifiers, thereby generating an enhanced per-device set of data;
  retrieving appointment data associated with a plurality of patients, the appointment data comprising patient check-in times, patient room assignments, patient roomed times, and patient check-out times;
  based on the patient roomed times, the patient check-out times, and the patient room assignments associating each patient of the plurality of patients with a patient location and with the health care clinician that corresponds to the device identifier colocated during time points between the patient roomed time and the patient check-out time;
  receiving patient data for each patient of the plurality of patients associated with the health care clinician from an electronic health records (EHR) system;
  training a predictive model by providing the clinician locations, patient locations, and patient data as training inputs to the predictive model, the predictive model comprising a plurality of discrete events representative of a clinical appointment including at least one event with a duration variably dependent on patient data, wherein a trained predictive model generates appointment durations and appointment slots as output;
  receiving an appointment request for a particular patient associated with the health care clinician, the appointment request corresponding to an appointment that is yet to occur;
  receiving the particular patient's patient data from the EHR system; and
  scheduling the appointment for the particular patient and the health care clinician an appointment duration determined by the trained predictive model.

14. The computer implemented method of claim 13, further comprising
  receiving time data for the plurality of patients associated with the health care providers, wherein the time data represents the health care providers active time within the EHR of each patient of the plurality of patients;
  identifying, based on the location information and the time data, a first subset of the time data and a second subset of the time data, the first set of time data representing the health care providers active time within the EHR and not in the presence of the patient, the second set of time data representing the health care providers active time within the EHR and within the presence of the patient; and
  wherein training the predictive model further utilizes the first subset of time data as input for the model.

15. The computer implemented method of claim 13, wherein scheduling the appointment comprises:
  accessing a set of available appointment durations or a set of available appointment slots;
  accessing patient data for the particular patient corresponding to input variables of the predictive model; and
  providing the predictive model the set of available appointment durations or the set of available appointment slots, and the patient data for the particular patient as inputs.

16. The computer implemented method of claim 13, wherein the appointment request comprises a preferred time, a reason for the appointment, or the identity of the patient.

17. The computer implemented method of claim 13, wherein the predictive model is a discrete event simulation model.

18. The computer implemented method of claim 13, wherein the patient data for training the predictive model comprise at least one of:
  an appointment type;
  a scheduled appointment duration;
  a reason for visit;
  a medication history;
  a clinician identifier or name;
  an indication of the patient's gender;
  a weight associated with the patient;
  a numerical indication of patient reported active problems;
  an indication of emergency room or urgent care visits;
  an indication of the patient's primary language; or
  a representation of a chronologic position of the appointment.

19. The computer implemented method of claim 13, wherein determining the appointment for the appointment duration by the trained predictive model comprises:
  receiving a set of available appointment durations or a set of available appointment slots;
  receiving patient data for the particular patient corresponding to the input variables of the predictive model; and
  providing the predictive model the set of available appointment durations or the set of available appointment slots, and the patient data for the particular patient as inputs.

20. The computer implemented method of claim 13, wherein the training inputs are determined by identifying Markov relationships between patient data and variations in patient appointments, variations in the duration of clinician-patient colocation, or variations in scheduled duration and actual duration.

* * * * *